US00PP22672P2

(12) United States Plant Patent
Stemkens

(10) Patent No.: US PP22,672 P2
(45) Date of Patent: Apr. 17, 2012

(54) *MIMULUS AURANTIACUS* PLANT NAMED 'MINREDDA'

(50) Latin Name: *Mimulus aurantiacus*
Varietal Denomination: Minredda

(75) Inventor: Henricus Godefridus Wilhelmus Stemkens, Enkhuizen (NL)

(73) Assignee: Syngenta Crop Protection AG, Basel (CH)

( * ) Notice: Subject to any disclaimer, the term of this patent is extended or adjusted under 35 U.S.C. 154(b) by 14 days.

(21) Appl. No.: 12/927,484

(22) Filed: Nov. 16, 2010

(51) Int. Cl.
*A01H 5/00* (2006.01)

(52) U.S. Cl. ..... Plt./454

(58) Field of Classification Search ..... Plt./454
See application file for complete search history.

*Primary Examiner* — Susan McCormick Ewoldt
(74) *Attorney, Agent, or Firm* — S. Matthew Edwards

(57) ABSTRACT

A new *Mimulus* plant named 'Minredda' particularly distinguished by the large, bold red flowers, medium yellow-green foliage that is relatively non-sticky when compared to most other *Mimulus* varieties commercially available with upright and tiered plant habit.

1 Drawing Sheet

Latin name of the genus and species of the plant claimed: *Mimulus aurantiacus*.

Varietal denomination: 'Minredda'.

BACKGROUND OF THE NEW PLANT

The present invention comprises a new *Mimulus*, botanically known as *Mimulus aurantiacus*, and hereinafter referred to by the variety name 'Minredda'.

'Minredda' is a product of a planned breeding program. The new cultivar has large, bold red flowers, darker yellow-green glossy foliage that is relatively non-sticky when compared to most other *Mimulus* varieties commercially available with upright and tiered plant habit.

'Minredda' originated from an open-pollinated hybridization made in July 2003 in Morgan Hill, Calif. The female parent was an unknown variety growing in a hobby garden. There are no known comparison statements to this female plant as the plant died before data was taken.

The male parent of 'Minredda' was an unknown variety. The resultant seed was sown in February 2004 in Gilroy, Calif. 'Minredda' was selected as one flowering plant within the progeny of the stated cross in the August 2004 in a controlled environment in Gilroy, Calif.

The first act of asexual reproduction of 'Minredda' was accomplished when vegetative cuttings were propagated from the initial selection in August 2004 in a controlled environment in Gilroy, Calif.

BRIEF SUMMARY OF INVENTION

Horticultural examination of plants grown from cuttings of the plant initiated in August 2004, and continuing thereafter, has demonstrated that the combination of characteristics as herein disclosed for 'Minredda' are firmly fixed and are retained through successive generations of asexual reproduction.

'Minredda' has not been observed under all possible environmental conditions. The phenotype may vary significantly with variations in environment such as temperature, light intensity and day length.

A Plant Breeder's Right for this cultivar has been applied for in Canada on Feb. 9, 2010 (No. 10-6825). 'Minredda' has not been made publicly available more than one year prior to the filing of this application.

The following traits have been repeatedly observed and are determined to be basic characteristics of the new variety. The combination of these characteristics distinguishes this *Mimulus* as a new and distinct variety.

BRIEF DESCRIPTION OF THE PHOTOGRAPHS

The accompanying photographic drawing shows typical flower and foliage characteristics of 'Minredda' with colors being as true as possible with an illustration of this type.

The photographic drawing shows a flowering plant of the new variety and a close-up of the flowers.

These photographs were taken in September 2009 of plants growing in a field trial in Gilroy, Calif.

DETAILED BOTANICAL DESCRIPTION

The plant descriptions and measurements were taken in late August 2010 under natural light. These plants were growing in field trials in Gilroy, Calif. These plants were about 20-22 weeks of age.

Color references are made to The Royal Horticultural Society Colour Chart (R.H.S.) 2001.

TABLE 1

DIFFERENCES BETWEEN THE NEW VARIETY 'MINREDDA' AND A SIMILAR VARIETY

| | 'Minredda' | *Mimulus aurantiacus puniceus* (a commercially available variety) |
|---|---|---|
| Plant habit: | Upright/tiered | Trailing |
| Flower size: | Larger | Smaller |
| Stickiness of foliage: | Relatively non-sticky | Very sticky |

Plant:

*Form, growth and habit.*—Upright, somewhat tiered and slightly open habit; removal of terminal apices (pinching) enhances branching habit.

*Plant height.*—50-55 cm.

*Plant height (inflorescence included).*—About 70 cm.

*Plant width.*—60 cm.

*Garden performance and tolerance to weather.*—Very good.

Roots:

*Number of days to initiate roots and develop roots.*—18-20 days at about 22 degrees C.

*Type.*—Fine, fibrous, free branching.

*Color.*—RHS N155B but whiter.

Foliage:

*Arrangement.*—Alternate, simple.

*Immature, leaf color, upper surface.*—Closest to RHS 146A but a little darker.

*Lower surface.*—RHS 146B.

*Mature, leaf color, upper surface.*—Darker than RHS 146A.

*Lower surface.*—RHS 146B.

*Length.*—4-5 cm.

*Width.*—1.3-1.5 cm.

*Shape.*—Elliptical.

*Base shape.*—Cuncate.

*Apex shape.*—Obtuste.

*Margin.*—Entire to very slightly serrulate.

*Texture, upper surface.*—Few glandular hairs.

*Lower surface.*—Few glandular hairs.

*Color of veins, upper surface.*—Indistinct.

*Color of veins, lower surface.*—RHS 145B.

Stem:

*Quantity of main stems per plant.*—5-6.

*Quantity of nodes per stem.*—12-15.

*Color of stem.*—RHS 144A overlaid with anthocyanins of between RHS 165A and RHS 165B.

*Length of stem.*—50-60 cm.

*Diameter.*—0.4 cm.

*Length of internodes.*—4.0-4.5 cm.

*Texture.*—Few glandular hairs.

*Color of pedicels.*—RHS 144A with some slight anthocyanins of about RHS 166C.

*Length of pedicels.*—0.8-1.0 cm.

*Diameter of pedicels.*—0.1 cm.

*Texture.*—Few glandular hairs.

Inflorescence:

*Type.*—On first flowering it appears to be a raceme, then matures to more of a panicle or thyrse; flowers are held somewhat horizontally to slightly upwards. With single axillary, salverform and zygomorphic flowers.

*Quantity of inflorescences per plant.*—About 100.

*Lastingness of individual blooms on the plant.*—12-14 days outside.

*Fragrance.*—None.

Bud (just when starting to show color):

*Color.*—RHS 180A.

*Length.*—3.7-4.7 cm.

*Width.*—0.6-1.0 cm.

*Shape.*—Oblong.

Immature inflorescence:

*Diameter.*—2.5-2.7 cm.

*Color, upper surface.*—RHS 45A.

*Lower surface.*—RHS 45D.

Mature inflorescence:

*Hortizontal diameter.*—3.2-3.7 cm.

*Vertical height.*—3.5-3.7 cm.

*Depth.*—5.0-5.5 cm.

Corolla:

*Color upper lobes, upper surface.*—RHS 45A, maturing to about RHS 44A with a hint of more orange.

*Color upper lobes, lower surface.*—RHS 45D to RHS 44D but slightly more grey.

*Length of upper lobes.*—1.6-1.7 cm.

*Width of upper lobes.*—1.0 cm.

*Color lateral lobes, upper surface.*—RHS 45A maturing to about RHS 44A with more orange.

*Color lateral lobes, lower surface.*—RHS 45D to RHS 44D but slightly more grey.

*Length of lateral lobes.*—1.7-1.8 cm.

*Width of lateral lobes.*—1.0 cm.

*Color lower mid-lobe, upper surface.*—RHS 45A maturing to about RHS 44A with more orange and patches of about RHS N25A basally.

*Color lower mid-lobe, lower surface.*—RHS 45D to RHS 44D but slightly more grey.

*Length of lower mid-lobe.*—1.5 cm.

*Width of lower mid-lobe.*—0.9-1.0 cm.

*Lobe (all) apex shape.*—Rounded to wide emarginate.

*Lobe (all) margin.*—Entire.

*Lobe (all) petal texture, all surfaces.*—Papillose.

*Corolla color, inside.*—RHS N155B with patches of RHS 24A.

*Corolla color, outside.*—RHS 12C basally with RHS 45C on the terminal end.

*Corolla tube length.*—4.0-4.2 cm.

Sepals:

*Quantity.*—5, mostly fused at the margins with slight free apices.

*Color, upper surface.*—Closest to RHS 144A but a little lighter green.

*Lower surface.*—Closest to RHS 144A but slightly more green.

*Length.*—2.6-2.7 cm.

*Width.*—Not observed due to fusion.

*Shape.*—Oblong.

*Apex shape.*—Acute.

*Based.*—Fused.

*Margins.*—Entire.

*Texture, upper surface.*—Few glandular hairs.

*Lower surface.*—Glandular hairs and a few dentritic hairs.

Reproductive organs:

*Pistil.*—1.

*Length.*—5.0 cm.

*Style color.*—RHS 155B.

*Style length.*—3.8 cm.

*Stigma color.*—RHS 155B.

*Stigma shape.*—Bi-parted.

*Ovary color.*—Closest to RHS N144C but lighter.

*Ovary length.*—0.7-0.8 cm.

*Ovary diameter.*—0.2 cm.

*Stamens.*—Quantity: 4.

*Color of filaments.*—RHS 15C.

*Length filaments.*—3.4-3.8 cm.

*Anther color.*—RHS 13B.

*Anther length.*—0.2 cm.

*Anther shape.*—Bi-lobed.

*Color of pollen.*—RHS 17A to RHS 17B.

*Pollen amount*.—Moderate.

*Fertility/seed set*.—Has not been observed on this hybrid.

Disease/pest resistance: Disease/pest resistance has not been observed on this hybrid.

What is claimed is:

1. A new and distinct variety of *Mimulus* plant named 'Minredda' substantially as illustrated and described herein.

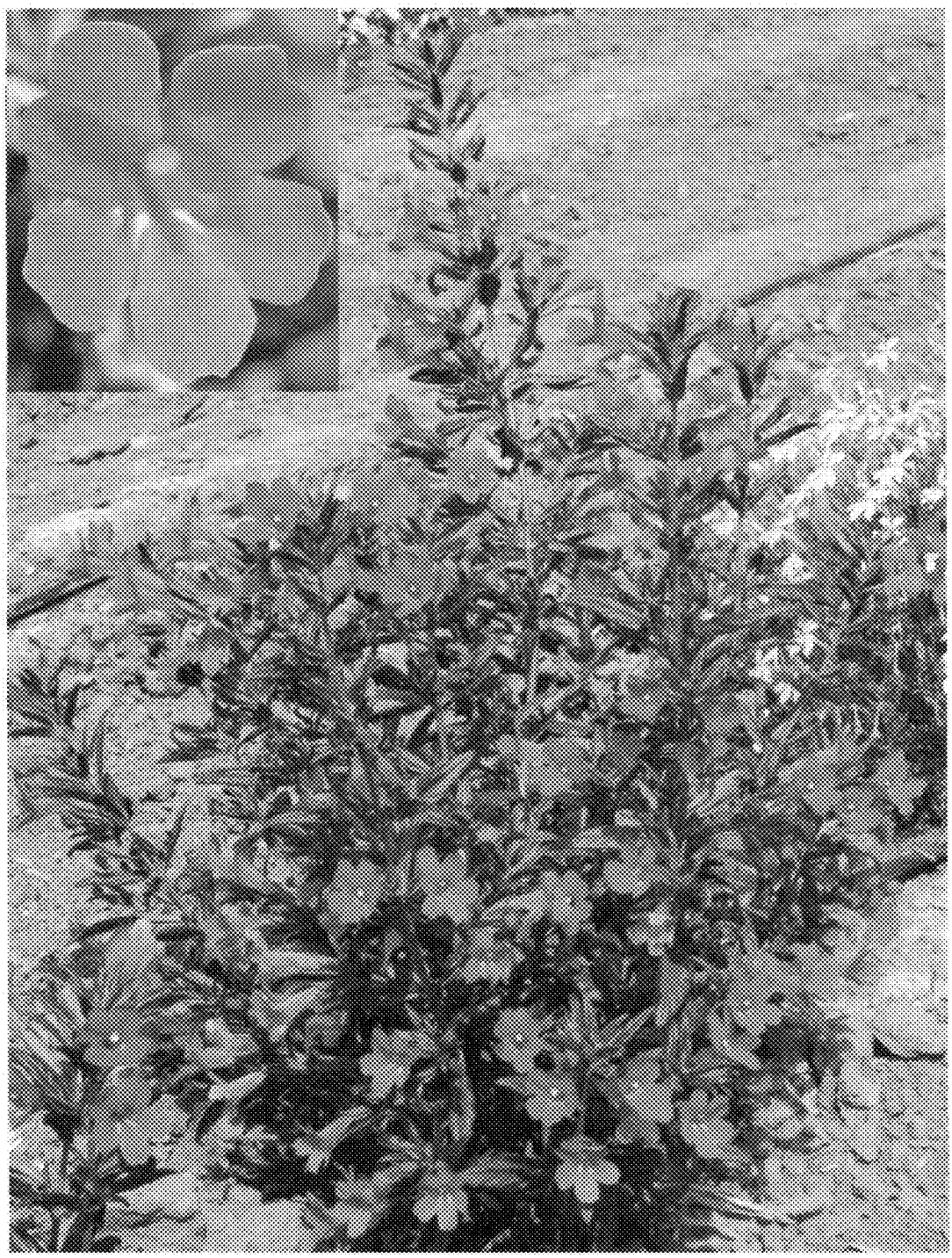

* * * * *